United States Patent [19]

Reynolds et al.

[11] Patent Number: 5,840,982

[45] Date of Patent: Nov. 24, 1998

[54] PROCESS FOR PREPARING PARA-PHENYLENEDIAMINE DERIVATIVES

[75] Inventors: Michael Reynolds; Russell E. Malz, both of Naugatuck, Conn.

[73] Assignee: Uniroyal Chemical Company, Inc., Middlebury, Conn.

[21] Appl. No.: 90,600

[22] Filed: Jun. 4, 1998

[51] Int. Cl.$^6$ .................................................. C07C 209/36
[52] U.S. Cl. .......................................... 564/423; 564/434
[58] Field of Search ...................................... 564/423, 434

[56] References Cited

U.S. PATENT DOCUMENTS

| | | | |
|---|---|---|---|
| 2,974,169 | 3/1961 | Newby et al. | 206/576 |
| 3,728,392 | 4/1973 | Levy et al. | 260/576 |
| 4,122,118 | 10/1978 | George et al. | 260/576 |
| 4,140,716 | 2/1979 | Maender et al. | 260/562 |
| 4,155,936 | 5/1979 | Sturm | 260/576 |
| 4,169,146 | 9/1979 | Katsube et al. | 424/248.4 |
| 4,187,248 | 2/1980 | Merten et al. | 260/576 |
| 4,187,249 | 2/1980 | Maender et al. | 260/576 |
| 4,196,146 | 4/1980 | Merten et al. | 260/576 |
| 4,209,463 | 6/1980 | Maender et al. | 260/576 |
| 4,313,002 | 1/1982 | Symon et al. | 564/423 |
| 4,479,008 | 10/1984 | Batorewicz et al. | 564/463 |
| 4,518,803 | 5/1985 | Batorewicz et al. | 564/410 |
| 4,614,817 | 9/1986 | Maender et al. | 564/406 |
| 4,670,595 | 6/1987 | Podder et al. | 564/406 |
| 4,683,332 | 7/1987 | Sturm | 564/414 |
| 5,117,063 | 5/1992 | Stern et al. | 564/398 |
| 5,420,354 | 5/1995 | Malz et al. | 564/423 |
| 5,574,187 | 11/1996 | Malz et al. | 564/402 |

FOREIGN PATENT DOCUMENTS

| | | |
|---|---|---|
| 0 184 914 A1 | 6/1986 | European Pat. Off. . |
| 61-171554 | 8/1986 | Japan . |
| 6-306020 | 11/1994 | Japan . |

OTHER PUBLICATIONS

Gerard V. Smith et al., "Hydrogenation of Nitrosobenzene over Palladium Catalysts," in *Catalysis of Organic Reactions*, Thomas A. Johnson and John R. Kosak, eds. (Marcel Dekker, New York, 1993), pp. 137–149.

Gerard V. Smith et al., "Hydrogenation and Dehydrohalogenation of p–Chloronitrobenzene: Effect of Pd Metal Particle Size on Activity and Selectivity," in *Catalysis of Organic Reactions*, Mike G. Scaros and Michael L. Prunier, eds. ((Marcel Dekker, New York, 1995), pp. 469–474.

*Primary Examiner*—Brian M. Burn
*Attorney, Agent, or Firm*—Raymond D. Thompson; Paul Grandinetti

[57] ABSTRACT

An improvement in a process for the preparation of a p-aminodiarylamine by reduction of the corresponding nitroso or nitro compound with hydrogen in a hydrogenator in the presence of a catalyst is disclosed. The invention includes equipping the hydrogenator with filtration means capable of separating the p-aminodiarylamine product from the catalyst, whereby the p-aminodiarylamine product can be removed from the hydrogenator while the catalyst is retained therein, thereby permitting the reaction to be run semicontinuously or continuously.

23 Claims, No Drawings

PROCESS FOR PREPARING PARA-PHENYLENEDIAMINE DERIVATIVES

BACKGROUND OF THE INVENTION

1. Field of the Invention

This invention relates to a method of preparing derivatives of para-phenylenediamines, such as p-aminodiphenylamine. More particularly, the invention relates to a method for the selective hydrogenation of an aqueous solution of an alkali metal or tetraalkylammonium salt of 4-nitrosodiphenylamine or 4-nitrodiphenylamine to produce p-aminodiphenylamine.

2. Description of Related Art

Para-phenylenediamine derivatives find a variety of utilities depending upon the para substituent. As an example, p-aminodiphenylamine is an important intermediate in the synthesis of rubber antioxidants and antiozonants for the prevention of polymer and rubber degradation. See Robert, "Rubber Compounding," reprinted from *Kirk-Othmer Encyclopedia of Chemical Technology*, Vol. 20 (John Wiley & Sons, 3$^{rd}$ Edition 1982). Other p-aminodiphenylamines, particularly $C_{5-10}$ alkyl-substituted derivatives thereof, are also useful in stabilizing rubbers.

The most accessible route to p-aminodiphenylamines involves N-nitrosation of a diphenylamine, rearrangement of the resulting N-nitrosodiphenylamine to the corresponding C-nitrosodiphenylamine or p-nitrosodiphenylamine and subsequent hydrogenation of the latter to the p-aminodiphenylamine.

p-Phenylenediamine derivatives have been commercially produced for a long time. Particularly, p-aminodiphenylamine has been manufactured by various batch processes. Included among these is the hydrogenation of aqueous solutions of alkali metal salts of 4-nitrosodiphenylamine in the presence of hydrogenation catalysts. For example, it is known to perform the hydrolysis in the presence of a palladium catalyst in a mixed solvent of hexanol and water.

U.S. Pat. No. 2,974,169 describes the reduction of an aqueous solution of an alkali metal salt of p-nitrosodiphenylamine with palladium on charcoal.

U.S. Pat. No. 4,313,002 discloses a method for preparing p-aminodiphenylamines from diphenylamines whereby neither the N-nitrosodiphenylamine nor the p-nitrosodiphenylamine intermediates need to be isolated. It is further disclosed that alkali metal salts of p-nitrosodiphenylamines are soluble in nonaqueous organic solvent systems consisting of certain aromatic hydrocarbons and saturated aliphatic alcohols and that such salts can be readily hydrogenated in their nonaqueous solutions to the corresponding p-aminodiphenylamine. The disclosure of this patent is hereby incorporated herein by reference.

U.S. Pat. No. 4,518,803 discloses a process for the preparation of p-nitrosodiphenylamine hydrochloride comprising reacting diphenylamine, a $C_5$–$C_{10}$ alkyl nitrite, and anhydrous HCl in the presence of a $C_5$–$C_{10}$ aliphatic alcohol and essentially in the absence of an aromatic solvent. The disclosure of this patent is hereby incorporated herein by reference.

Another way to make p-phenylenediamine derivatives, such as p-aminodiphenylamine, is by batch hydrogenation as taught in Japanese patent public disclosure 6-306020 (patent application Ser. No. 5-95855) by Katayama et al. In this case, p-nitrosodiphenylamine is added to a batch vessel slowly and hydrogenated continuously until the vessel is full. Katayama et al. state that they obtain higher yields over the earlier batch reactions. Even if somewhat higher yields were obtained by this method, there remains a need for still higher yields as well as increased production capabilities.

There have been several recent patents (U.S. Pat. Nos. 5,117,063; 5,420,354; and 5,574,187) concerning new routes to p-aminodiphenylamine. These patents offer useful background routes for the process of producing substituted p-phenylenediamines.

The invention relates, inter alia, to an improvement in a process for the production of p-aminodiphenylamine by hydrogenation of an aqueous solution of p-nitrosodiphenylamine alkali metal salt, an aqueous solution of p-nitrosodiphenylamine tetraalkylammonium salt, or a solution of p-nitrophenylamine in the presence of a hydrogenation catalyst such as the process described in European Patent Publication 184914 as well as in Japanese public disclosure No. 6-306020, referred to above. There are several routes known in the art for producing such solutions. A derivative of aniline can be reacted with p-chloronitrobenzene to produce p-nitrodiphenylamine, as in U.S. Patent Nos. 4,122,118; 4,140,716; 4,155,936; 4,187,248; 4,187,249; 4,196,146; 4,209,463; 4,614,817; 4,670,595; and 4,683,332. Subsequent hydrogenation of the p-nitrodiphenylamine yields p-aminodiphenylamine.

Those skilled in the art will understand that p-nitrosodiphenylamine and p-nitrodiphenylamine are but single members of the classes of C-nitrosodiarylamines and C-nitrodiarylamines, respectively, and as used herein it is intended that any reference to them should be taken as a reference to their entire classes. Similarly, reference to N-nitrosodiphenylamine is intended to be a reference to the class of N-nitrosodiarylamines and reference to p-aminodiphenylamine is a reference to the class of p-aminodiarylamines. p-Nitrosodiphenylamine and solutions of the salts thereof can be prepared by the reaction of diphenylamine and an alkyl nitrite in the presence of excess hydrogen chloride, as in U.S. Pat. Nos. 4,518,803 and 4,479,008. The products can then be hydrogenated to produce p-aminodiphenylamine.

The subsequent batch hydrogenation of aqueous solutions of p-nitrosodiphenylamine alkali metal salt or p-nitrosodiphenylamine tetraalkylammonium salt, or solutions of p-nitrodiphenylamine are not quantitative. Typically, the hydrogenations of nitro and nitroso compounds yield unwanted by-products resulting in yield losses, higher manufacturing costs, waste disposal, and an environmentally undesirable process. Details of the mechanism of production of these unwanted by-products and waste tars are described in Gerard V. Smith et al., *Hydrogenation of Nitrosobenzene over Palladium Catalysts* in *Catalysis of Organic Reactions*, T. A. Johnson and J. R. Kosak, eds. (Marcel Dekker 1993), pp. 137–49.

There are numerous patents and literature references relating to the batch hydrogenations of nitro and nitroso compounds. However, these batch reactions suffer from the side reactions mentioned above. The invention is directed to a semicontinuous or continuous process to improve the yield over standard batch hydrogenations, limit production costs, eliminate environmentally undesirable waste tars, and gain a savings in catalyst usage.

There is a need for a process that will enable the production of derivatives of p-phenylenediamine in high yield using a batch reactor and a specified amount of product per cycle. It is desirable to enable the production of large quantities of product with minimal loading and unloading of the reactor. It is also desirable to minimize capital expenditures for new equipment and minimize waste and byproduct formation, both advantageous in a commercial process.

Accordingly, one object of the invention is to provide a method for producing such p-phenylenediamine derivatives using standard batch hydrogenation equipment with only minor modifications. A further object is to produce p-aminodiphenylamine in sufficient quantity and yield to be commercially practical. A still further object is to decrease cycle time for the production of p-aminodiphenylamine. An even further object is to increase production and minimize waste and capital expenditure on new equipment.

SUMMARY OF THE INVENTION

It has been found that by modifying the equipment of a standard hydrogenator, a batch reaction may be changed to an extended batch (as employed herein, the terms "extended batch" and "semicontinuous" are intended to be synonymous) or continuous production process. A batch reactor produces a set amount of product per cycle, and significant amounts of time are required to load and unload the reactor. The invention permits increases in the amount of product with only one loading and unloading cycle of the reactor.

More particularly, the invention is directed to an improvement in a process for the preparation of a p-aminodiarylamine by reduction of the corresponding nitroso or nitro compound with hydrogen in a hydrogenator in the presence of a catalyst, wherein the improvement comprises equipping the hydrogenator with filtration means capable of separating the p-aminodiarylamine product from the catalyst, whereby the p-aminodiarylamine product can be removed from the hydrogenator while the catalyst is retained therein, thereby permitting the reaction to be run semicontinuously or continuously.

DETAILED DESCRIPTION OF THE INVENTION

By equipping a standard hydrogenator with a means of maintaining the catalyst in the vessel, the reactant, e.g., sodium salt of p-nitrosodiphenylamine, can be pumped in and the catalyst-free product, e.g., p-aminodiphenylamine, continuously removed. The process can continue until the catalyst charge deactivates, at which time the hydrogenation reaction stops.

For the extended batch or continuous process of the invention, a larger charge of catalyst is used than is normally employed in a standard batch process to ensure sufficiently large, commercially viable production quantities. The invention allows up to a 50 percent reduction in total cycle time and an increase of over 65 percent in the amount of product per run.

In a heterogeneous catalytic hydrogenation, several important variables are critical. These variables must be controlled and optimized in order to achieve a successful commercial process. In a stirred reactor system, one of these variables is the cycle time for the reaction. Another important variable, for all types of reactors, is the product yield, which is closely related to the generation of side products.

In a conventional batch heterogeneous catalytic hydrogenation reaction, the reactants and catalyst are first loaded into a reactor. Next, the vessel is purged of oxygen, after which it is pressurized with hydrogen. At this point, the reactor is heated, with agitation, to the desired temperature, and the reaction is continued to completion. The completion of the reaction corresponds to the cessation of hydrogen gas uptake.

At this point, the vessel is cooled and vented. The catalyst is then separated from the reaction mixture, which is then processed to give the desired product.

There is a significant exotherm during the reaction of p-nitrosodiphenylamine to produce p-aminodiphenylamine. If the reaction is allowed to proceed above reaction temperature for any time whatsoever, the p-nitrosodiphenylamine will hydrolyze to yield lower amounts of the desired p-aminodiphenylamine product. In addition, the high concentration of p-nitrosodiphenylamine allows it to condense with the intermediate hydroxylamine, thus decreasing the yield of the desired product and forming undesirable side products.

According to the invention, the reaction of p-nitrosodiphenylamine to produce p-aminodiphenylamine is carried out by a process that allows loading and maintaining several times the catalyst level used in a conventional batch reactor of the type described above. The vessel may be loaded with finished product or solvent. Fresh reactant may be continuously pumped in while finished product is taken off.

The invention is an improved process in terms of greater yield of desired product, reduced cycle time, and reduction of side products. More specifically, it improves productivity in the following manner: The standard procedure involves a load time of one hour, a reaction time of two hours, and a cooling time of one hour, for an overall cycle time of five hours per batch, or 40 hours for eight batches. The process of the invention achieves the same level of production as follows: Load the reactor for one hour with an eightfold increase in the amount of catalyst, which is kept in the vessel. Pump eight batch-sized charges of reactant over the catalyst over a period of 16 hours. Cool the contents of the vessel for one hour, and filter the catalyst for one hour. This process gives an overall reaction cycle time of 19 hours, which is less than half the 40 hours for the standard procedure detailed above.

In this invention, a lower and more controlled reaction temperature can be maintained, resulting in reduced hydrolysis and an increased overall yield of the desired product. Likewise, the yield of side condensation products, which diminish the yield of the desired end product, decreases because of the limited concentration of nitro or nitroso compounds in the reaction vessel.

Although the method described herein is especially applicable to the preparation of p-aminodiphenylamine because of its industrial importance, the method is broadly applicable to the class of p-aminodiphenylamines. Thus, this method is applicable to diphenylamines substituted on one or more rings with, for example, alkyl, alkoxy, halogen, and the like. Examples of suitable diphenylamines include 2-alkoxy-, 2,2'-dialkoxy-, and 2,4'-dialkoxydiphenylamines, where the alkoxy group can be branched or straight and may be methoxy, ethoxy, propoxy, butoxy, pentoxy, isomers thereof, and the like, and corresponding phenoxy and benzyloxy analogs; similarly substituted halodiphenylamines, where the halogen may be fluorine, chlorine, bromine, or iodine; and 2-alkyl-, 2,2'-dialkyl-, and 2,4'-dialkyldiphenylamines, where the alkyl group may be methyl, ethyl, propyl, butyl, pentyl, hexyl, decyl, hexadecyl, isomers thereof, and the like.

Among the organic solvents that can be used in the practice of the invention are aliphatic and aromatic hydrocarbons, saturated aliphatic alcohols and ethers, glycols, such as ethylene glycol and polyethylene glycol, monoethers of the glycols, and mixtures thereof. An essential limitation upon the organic solvents is that they be unreactive under the conditions of the described process. Toluene is preferred.

Nitrosation of diphenylamine may be effected by conventional means, as exemplified in U.S. Pat. No. 3,728,392, or in nonaqueous organic media, such as water-insoluble saturated aliphatic alcohols or mixtures of aromatic compounds and aliphatic alcohols.

Rearrangement of the N-nitrosodiphenylamine to p-nitrosodiphenylamine is effected by contacting the N-nitrosodiphenylamine solution with a mineral acid, e.g., a hydrogen halide. Hydrogen chloride is preferred. The hydrogen halide may be used in from 1 to about 5 molar proportions, based on the diphenylamine, with the range of 1.2 to 1.8 being preferred. Generally, the rearrangement is carried out at a temperature below about 70° C.

Where the N-nitrosodiphenylamine is prepared by conventional methods, it is first dissolved in an aromatic solvent having a boiling point between about 80° and about 160° C. Examples of such solvents include benzene, toluene, ethylbenzene, and the xylenes. Thereafter, the solution containing the N-nitrosodiphenylamine is mixed with a solution of the hydrogen halide in a saturated primary or secondary aliphatic alcohol containing up to about 10 carbon atoms. Examples of such alcohols include methanol, ethanol, propanol, butanol, pentanol, hexanol, heptanol, octanol, nonanol, decanol, isomers thereof, and the like. Preferred alcohols include 1-butanol, 1-hexanol, and 2-ethylhexanol. Generally, about equal weights of the aromatic compound and the aliphatic alcohol are used, although this is not critical.

In an alternative procedure, formation of the N-nitrosodiphenylamine and its rearrangement to the p-nitrosodiphenylamine can occur concurrently. Typically, sodium nitrite is added to a solution of the diphenylamine in an aromatic solvent, as described above, followed by a solution of the hydrogen halide in a saturated aliphatic alcohol. Enough hydrogen halide is present to provide about two to about five molar proportions based on diphenylamine. Approximately equal amounts by weight of the aromatic solvent and the aliphatic alcohol are used, although this use is not critical. Among the preferred alcohols, which are saturated aliphatic alcohols containing up to about 10 carbon atoms, as described above, are methanol, 1-butanol, 1-hexanol, and 2-ethylhexanol. The saturated aliphatic alcohols, both here and above, may, if desired, be replaced by similar aliphatic ethers.

There are at least two known routes for the preparation of nitrodiphenylamine. One method is disclosed in U.S. Pat. No. 5,117,063, which describes the production of both nitro- and nitroso-diphenylamine. A second method is the reaction of aniline with para-nitrochlorobenzene. This chemistry is discussed in the Related Art section of U.S. Pat. No. 5,117,063.

The next step in this process is the conversion of the rearrangement product to its alkali metal or tetraalkylammonium salt. The p-nitrosodiphenylamine is present after rearrangement at least in part as its mineral acid salt. The mixture is then contacted with an aqueous solution of a base of an alkali metal or a tetraalkylammonium compound. Examples of suitable alkali metal bases include the hydroxides and carbonates of lithium, sodium, potassium, cesium, and rubidium. Sodium and potassium are the preferred cations, with sodium being most preferred. Where a tetraalkylammonium compound is used, the alkyl groups can be the same or different and can be branched or straight. Although the number of carbon atoms in the alkyl groups is not critical, there will generally be no more than 10, i.e., methyl, ethyl, propyl, butyl, pentyl, hexyl, heptyl, octyl, nonyl, decyl, and isomers thereof. The concentration of the base may be up to about 25 percent by weight, but normally it is in the range of about 5 to about 20 percent by weight. The amount of base employed is equivalent to about 0.5 to about 1.5 molar proportions in excess of the amount of hydrogen halide used for rearrangement. For example, if 3 molar proportions of hydrogen halide is used in the rearrangement, then from 3.5 to about 4.5 molar proportions of base are used. This use is necessary to neutralize the excess acid, convert the salt of p-nitrosodiphenylamine to its free base, and then convert the free base to its salt.

Because the alkali metal and tetraalkylammonium salts of p-nitrosodiphenylamines are soluble in the organic solvent system used, a two-phase system is present at this stage with the nonaqueous phase consisting largely of a salt of p-nitrosodiphenylamine dissolved in the nonaqueous organic solvent and an aqueous organic phase consisting largely of inorganic salts dissolved in water.

The ultimate step in this process is the hydrogenation of the nonaqueous organic phase, which consists largely of the alkali metal or tetraalkylammonium salt of p-nitrosodiphenylamine. Hydrogenation is conducted at pressures in excess of atmospheric, for example, up to about 5000 psig, but generally pressures up to about 1000 psig are sufficient. Pressures in the range of about 100 to about 500 psig are preferred. Hydrogenation temperatures may range up to about 200° C. Depending upon the catalyst used and the pressure employed, temperatures less than about 150° C will generally suffice. Temperatures less than 100° C, preferably about 50° to about 75° C, will often be adequate.

A wide range of catalysts known in the art can effect the desired reduction. Examples of suitable catalysts include palladium, platinum, nickel, rhenium, rhodium, ruthenium, and copper chromite. Palladium is preferred. Such catalysts may be used either supported or unsupported. If supported, they may be used on such supports as charcoal, kieselguhr, alumina, silica, and the like. Charcoal (i.e., carbon) and kieselguhr are preferred.

The practice of the invention is basically dependent upon the filtration of the reactor contents, which allows continuous removal of catalyst-free product from the reaction vessel with retention of the catalyst. This action can be accomplished by any of several designs of filtration means. For example, the reactor can have a dip tube inserted into the reactor contents. At the end of the dip tube, a filtration is device is installed so that continuous removal of the catalyst-free product can be accomplished. With a proper filtration system, the correct level of catalyst can be maintained in the reactor. The continuous filtration system coupled with the feeding-in of additional reactant keeps the process going until completion.

The filtration device can be constructed of several materials, including, but not limited to, sintered metal filters, woven metal, a combination of woven metal and fabric, and other suitable materials. Filter size and porosity are determined by the flow, catalyst size, the process stream being filtered, and other operating parameters. Optimization for a particular system can be readily determined by those skilled in the art, without undue experimentation.

Several designs of filters can be utilized, such as tube bundles, plate and frame, leaf filters, rotary leaf filters, and the like. The filter may be a fully continuous filter where the catalyst and product are returned to the reactor, while a portion of catalyst-free product is removed. The fully continuous system can utilize backflushing of the filter with catalyst-free product, gas, or a combination of both. Where gas is used, hydrogen is preferred. Backflushing with hydrogen does not reduce the concentration of hydrogen in the system and thus will not dilute the reactor as would be the case if an inert gas, such as nitrogen, were used. However, depending upon the amount of gas used for backflushing, an inert gas, such as nitrogen, could be used without detrimental effects. This action will help to ensure that all the catalyst remains in the reactor with the reaction media, rather than being bound to the filter element. The filter may also be a closed element where catalyst collects for a small period of time and is backflushed periodically to return the catalyst to the reactor.

The preferred method of filtration is to install a recirculation loop onto the reactor. The reactor contents, essentially product, are removed continuously and passed through a filtration system. The catalyst and some of the product are returned to the reactor, while a portion of catalyst-free product is removed. The correct level of catalyst is maintained in the reactor by means of the filtration system of the invention. The continuous filtration system coupled with feeding in additional reactant keeps the process going until completion.

Various features and aspects of the invention are illustrated further in the examples that follow. While these examples are presented to show to one skilled in the art how to operate within the scope of the invention, they are not intended in any way to serve as a limitation upon the scope of the invention.

COMPARATIVE EXAMPLE A

Batch Reduction of p-Nitrosodiphenylamine, Sodium Salt to p-Aminodiphenylamine

237 Grams of an 18 percent solution of p-nitrosodiphenylamine, sodium salt; 63 grams of toluene; and 0.062 gram of dry Pd/C catalyst were charged to a one-liter Hastelloy C autoclave at 60° C. and 200 psig hydrogen. After continuing the reaction for one hour, it was found that p-aminodiphenylamine was produced in 97 percent yield.

EXAMPLES 1–4

Extended Batch Reduction of p-Nitrosodiphenylamine, Sodium Salt to Produce p-Aminodiphenylamine Each of these examples relates to a reaction that was completed at 60° C. using a one-liter Hastelloy autoclave pumping a continuous feed of p-nitrosodiphenylamine, sodium salt and toluene, with removal of product via a dip tube. The Pd/C catalyst was kept in the vessel by means of a sintered metal filter on the dip tube. Hydrogen was fed continuously via a liquid level controller and back pressure regulator.

Yield data on Examples 1–4 may be found in Table 1. For Examples 1 and 2, the sampling system leaked at the pump head on the autoclave sampling system. The reported yields are therefore estimated, based on the amount of recovered material.

TABLE 1

EXTENDED BATCH REDUCTION

| Example | Plant Catalyst Level | Reactant[1] Pumped (Batches) | Yield % | Yield % Based on Conversion |
|---|---|---|---|---|
| 1 | 3× | 3.2× | 93 | 99 |
| 2 | 3× | 3.2× | 85 | 95 |
| 3 | 3× | 4.9× | 50 | 77 |
| 4 | 3× | 4.1× | 76 | 85 |

[1]The reactant in all the examples is p-nitrosodiphenylamine, sodium salt.

In Examples 2, 3, and 4, some aniline was formed as an unwanted by-product. In Example 2, the amount of aniline formed was approximately 0.01 pound per pound of p-aminodiphenylamine product. In Example 3, the amount was 0.20 pound per pound of p-aminodiphenylamine. In Example 4, the amount of aniline formed was approximately 0.13 pound per pound of p-aminodiphenylamine.

The data in Table 1 demonstrate the utility of the process of the invention as long as the amount of p-nitrosodiphenylamine, sodium salt/toluene pumped to the vessel does not exceed the catalyst level. These data demonstrate the selectivity of the process. Examples 3 and 4 produced more aniline when the catalyst became inactivated by pumping too much p-nitrosodiphenylamine, sodium salt/toluene. Examples 1 and 2, run on a 1:1 basis of catalyst:p-nitrosodiphenylamine, sodium salt demonstrate low by-product formation.

COMPARATIVE EXAMPLE B

Comparative Example A was repeated. This time the product yield was quantitative.

EXAMPLES 5–6

Extended Batch Reduction of p-Nitrosodiphenylamine, Sodium Salt to Produce p-Aminodiphenylamine: The Effect of Pump Rate on Yield of p-Aminodiphenylamine Using the same equipment and essentially the same process as described for Comparative Example A and Examples 1 to 4, another set of experiments was conducted. The distinction in this set of experiments was that the p-nitrosodiphenylamine, sodium salt was delivered by pump at twice the normal rate, which is one batch per hour. All four batches were pumped into the autoclave in approximately two hours. The lower than expected yields for this series can be seen in Table 2.

TABLE 2

EXTENDED BATCH REDUCTION

| Example | Plant Catalyst Level | Reactant Pumped (Batches) | Yield % |
|---|---|---|---|
| 5 | 6× | 4× | 65 |
| 6 | 6× | 4× | 69 |

COMPARATIVE EXAMPLE C

Comparative Example A was repeated except that only 0.021 gram of dry 5 percent Pd/C catalyst was used. The product yield was again quantitative.

EXAMPLES 7–9

Extended Batch Reduction of p-Nitrosodiphenylamine, Sodium Salt to Produce p-Aminodiphenylamine All experiments were carried out at 60° C. using a one-liter Hastelloy C autoclave pumping a continuous feed of an 18 percent aqueous solution of p-nitrosodiphenylamine, sodium salt and toluene (237 grams of p-nitrosodiphenylamine, sodium salt; 63 grams of toluene) with removal of product via filtration means comprising a dip tube. The catalyst remained in the vessel due to a sintered metal filter on the dip tube. Hydrogen was fed continuously via a mass flow controller, maintaining 200 psig using a liquid level controller and back pressure regulator. All experiments used a five percent Pd/C catalyst.

The 18 percent aqueous solution of p-nitrosodiphenylamine, sodium salt was delivered by pump at the rate of about one batch per hour (one batch is 237 grams of an 18 percent aqueous solution of p-nitrosodiphenylamine and 63 grams of toluene). This rate was actually about 17 percent faster than the normal batch reaction rate (normal rate is 237 grams of an 18 percent aqueous solution of p-nitrosodiphenylamine and 63 grams pumped per hour). The results are shown in Table 3. As can be noted in Table 3, the yield data for Examples 7 and 9 are greater than quantitative and thus obviously incorrect. This incorrect result was due to weighing errors. However, the yields were substantially quantitative and no appreciable amounts of unreacted p-nitrosodiphenylamine, sodium salt or impurities were detected.

TABLE 3

EXTENDED BATCH REDUCTION

| Example | Plant Catalyst Level | Reactant Pumped (Batches) | Yield % | Yield % Based on Conversion |
|---------|---------------------|---------------------------|---------|------------------------------|
| 7 | 6× | 4× | 96 | 105 |
| 8 | 6× | 4× | — | — |
| 9 | 6× | 6× | 99 | 101 |

These data clearly demonstrate higher production rates and yield of p-aminodiphenylamine as compared to a standard batch hydrogenation. A solution of p-nitrosodiphenylamine, sodium salt/toluene was pumped to the hydrogenator and equipped with a filter at the end of a dip tube, and product was continuously removed. Slightly less p-nitrosodiphenylamine, sodium salt/toluene solution than catalyst was pumped, the actual weight ratio being 1.5:1 catalyst:p-nitrosodiphenylamine. The weight ratio numbers are derived from a 6× catalyst level being divided by 4× batches. 1× catalyst level is the amount (weight) of catalyst used to reduce 1× standard batch (vessel, charge) reaction. Examples 7 and 8 demonstrate approximately a 50 percent reduction in the total time to produce the same amount of product on a batchwise basis. Example 9 demonstrates an even greater time savings. All three examples demonstrate low by-product formation, which corresponds to higher yields. The large amount of materials resulted in weights that gave yields over 100 percent.

EXAMPLE 10

Extended Batch Reduction of p-Nitrosodiphenylamine, Sodium Salt to Produce p-Aminodiphenylamine: The Effect of High Catalyst Level and p-Nitrosodiphenylamine, Sodium Salt Batches This experiment was carried out at 60° C. using a one-liter Hastelloy C autoclave pumping a continuous feed of an 18 percent aqueous solution of p-nitrosodiphenylamine, sodium salt and toluene (237 grams of p-nitrosodiphenylamine, sodium salt; 63 grams of toluene) with removal of product via filtration means comprising a dip tube. The catalyst remained in the vessel due to a sintered metal filter on the dip tube. Hydrogen was fed continuously via a mass flow controller, maintaining 200 psig using a liquid level controller and back pressure regulator. A five percent Pd/C catalyst was used. It will be noted that this experiment was run in the same manner as those described above, but the results appear to be poorer. Analysis indicated no appreciable sign of impurities. However, the sampling system leaked during the reaction. Only enough material was recovered to obtain an 86 percent yield. It was concluded, from the analysis and the lack of detection of any side products, that the experiment was successful.

TABLE 4

EXTENDED BATCH REDUCTION

| Example | Plant Catalyst Level | Reactant Pumped (Batches) | Yield % | Yield % Based on Conversion |
|---------|---------------------|---------------------------|---------|------------------------------|
| 10 | 15× | 12× | 86% | — |

These data demonstrate that decreasing the catalyst:p-nitrosodiphenylamine, sodium salt/toluene ratio results in incomplete reaction.

In view of the many changes and modifications that can be made without departing from principles underlying the invention, reference should be made to the appended claims for an understanding of the scope of the protection to be afforded the invention.

What is claimed is:

1. In a process for the preparation of a p-aminodiarylamine by reduction of the corresponding nitroso or nitro compound with hydrogen in a hydrogenator in the presence of a catalyst, the improvement that comprises equipping the hydrogenator with filtration means capable of separating the p-aminodiarylamine product from the catalyst, whereby the p-aminodiarylamine product can be removed from the hydrogenator while the catalyst is retained therein, thereby permitting the reaction to be run semicontinuously or continuously.

2. The process of claim 1 wherein the p-aminodiarylamine is p-aminodiphenylamine.

3. The process of claim 2 wherein the p-aminodiphenylamine is prepared by the reduction of an alkali metal salt of p-nitrosodiphenylamine.

4. The process of claim 2 wherein the p-aminodiphenylamine is prepared by the reduction of a tetraalkylammonium salt of p-nitrosodiphenylamine.

5. The process of claim 2 wherein the p-aminodiphenylamine is prepared by the reduction of p-nitrodiphenylamine.

6. The process of claim 1 wherein the filtration means comprises a filtration device constructed from sintered metal, woven metal, or a combination of woven metal and fabric.

7. The process of claim 7 wherein the filtration means further comprises a dip stick to which the filtration device is attached.

8. The process of claim 1 wherein the catalyst is present in the hydrogenator in a concentration greater than that employed in the reaction when run batchwise.

9. The process of claim 1 wherein the catalyst is selected from the group consisting of palladium, platinum, nickel, rhenium, rhodium, ruthenium, and copper chromite.

10. The process of claim 9 wherein the catalyst is supported on carbon, kieselguhr, alumina, or silica.

11. The process of claim 9 wherein the catalyst is palladium.

12. The process of claim 11 wherein the palladium is supported on carbon.

13. The process of claim 1 carried out in the presence of at least one solvent selected from the group consisting of aliphatic hydrocarbons, aromatic hydrocarbons, saturated aliphatic alcohols, saturated aliphatic ethers, glycols, monoethers of glycols, and mixtures thereof.

14. The process of claim 13 wherein at least one solvent is an aromatic hydrocarbon.

15. The process of claim 14 wherein at least one solvent is toluene.

16. The process of claim 1 wherein the hydrogenation is carried out at a pressure in the range of from about 100 to about 500 psig.

17. The process of claim 16 wherein the hydrogenation is carried out at a pressure of about 200 psig.

18. The process of claim 1 wherein the hydrogenation is carried out at a temperature in the range of from about 50° C. to about 75° C.

19. The process of claim 18 wherein the hydrogenation is carried out at a temperature of about 60° C.

20. The process of claim 1 wherein the filtration means is a fully continuous system.

21. The process of claim 20 wherein the fully continuous system can utilize backflushing of the filter with catalyst-free product, gas, or a mixture thereof.

22. The process of claim 1 wherein the filtration means comprises a recirculation loop installed onto the reactor to provide means for reactor contents to be removed continuously and passed through a filtration system whereupon the catalyst and a portion of the product are returned to the reactor and a portion of the catalyst-free product is removed, whereby the correct level of catalyst is maintained in the reactor.

23. In a process for the preparation of p-aminodiphenylamine by reduction of p-nitrosodiphenylamine, sodium salt with hydrogen in a hydrogenator in the presence of a catalyst, the improvement that comprises:

(a) equipping the hydrogenator with filtration means capable of separating the p-aminodiarylamine product from the catalyst, whereby the p-aminodiarylamine product can be removed from the hydrogenator while the catalyst is retained therein, thereby permitting the reaction to be run semicontinuously or continuously, said filtration means comprising a recirculation loop installed onto the reactor to provide means for reactor contents to be removed continuously and passed through a filtration system whereupon the catalyst and a portion of the product are returned to the reactor and a portion of the catalyst-free product is removed, whereby the correct level of catalyst is maintained in the reactor;

(b) employing palladium supported by carbon as the catalyst; and (c) running the reaction under a pressure of about 200 psig and at a temperature of about 60° C. in the presence of toluene.

* * * * *